United States Patent [19]

Havstad et al.

[11] 4,143,872

[45] Mar. 13, 1979

[54] LUNG VOLUME EXERCISER

[75] Inventors: Harold R. Havstad, Eagle Point, Oreg.; Miguel A. Ruksenas, Fallbrook; Robert O. Rowland, Hemet, both of Calif.

[73] Assignee: Hudson Oxygen Therapy Sales Company, Temecula, Calif.

[21] Appl. No.: 785,685

[22] Filed: Apr. 7, 1977

[51] Int. Cl.² .............................................. A61B 5/08
[52] U.S. Cl. .............................. 272/99; 272/DIG. 5; 128/2.08
[58] Field of Search .......................... 272/99, DIG. 5; 128/2.08, DIG. 29; 73/379

[56] References Cited

U.S. PATENT DOCUMENTS

| 393,869 | 12/1888 | Warren | 272/99 X |
|---|---|---|---|
| 1,176,886 | 3/1916 | Ermold | 128/209 X |
| 3,669,097 | 6/1972 | Fitz | 272/99 |
| 3,754,546 | 8/1973 | Cooper | 272/99 X |
| 3,922,525 | 11/1975 | Kozak | 128/2.08 X |
| 4,025,070 | 5/1977 | McGill | 128/2.08 X |

Primary Examiner—Richard J. Johnson
Attorney, Agent, or Firm—Seiler & Quirk

[57] ABSTRACT

A device for exercising the lungs by forced inhaling or exhaling comprises a mouthpiece and a valve assembly incorporating a valve housing unit having a gas inlet port and a gas outlet port both communicating with a cavity in which a movable valve body is received and which valve body has a first passageway for directing gas between the inlet and outlet ports and a second passageway for directing gas between a by-pass port and the gas outlet port. The relative amount of gas passing through the gas inlet port and through the gas by-pass port is determined by the position of the valve body and can be regulated by moving the valve body. The device also includes means for monitoring the flow of gas passing through the gas inlet port and preferably the length of time of that gas passage, and means for counting sequential inspirations or expirations of the user during the exercise.

7 Claims, 8 Drawing Figures

LUNG VOLUME EXERCISER

BACKGROUND OF THE INVENTION

Various devices and instruments have been proposed for exercising the lungs in order to increase lung capacity and improve pulmonary functions. Such devices usually require the patient to exhale or inhale through a mouthpiece, and often incorporate some visible means for observing the capacity of the participant, for example, by a meter or an article that is displaced by passage of gas through the device as the user exhales or inhales. Preferably, the visible means is one which can be observed by the user which will tend to increase participation and interest in the exercise.

SUMMARY OF THE INVENTION

The present device utilizes a unique valve assembly for determining gas flow through the valve in order to displace a movable member, which movement is detected for monitoring the results of the exercise. The device includes a valve assembly for determining and varying the amount of air for displacing the movable member. Such a feature allows an operator to increase or decrease the difficulty of the exercise whereby the lung volume capacity may be gradually increased, pulmonary functions improved and in strengthening the bodily functions in order to achieve improved respiratory characteristics and efficiency. The device is simple to operate, and the mouthpiece and valve assembly construction is of a relatively simple but highly effective and efficient design thereby significantly improving the ease of manufacture, assembly and use.

DETAILED DESCRIPTION OF THE INVENTION

Figure 1:
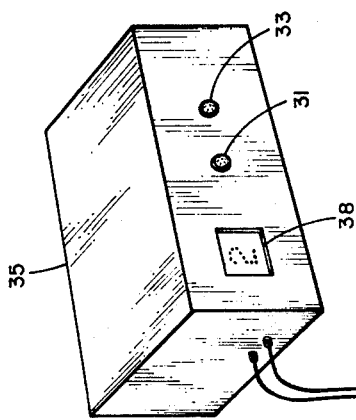
FIG. 1 is a perspective view of the device, partly cut away to illustrate components thereof.
Figure 1:
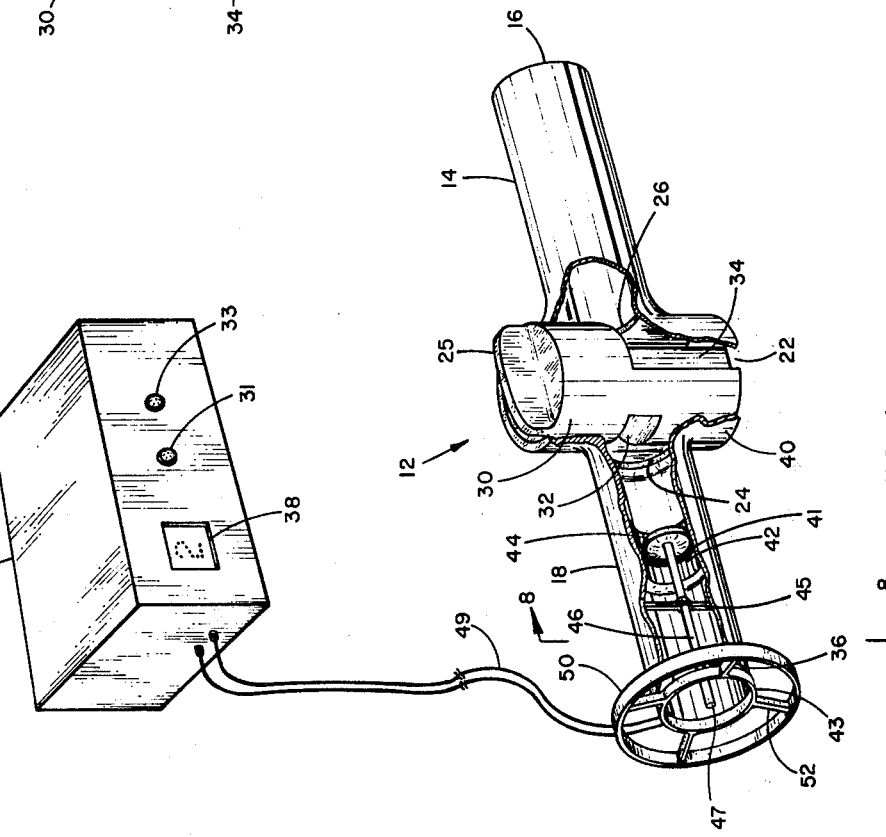
Figure 8:
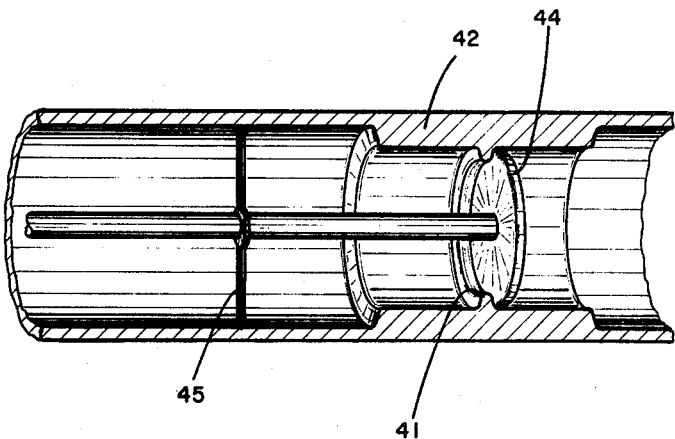
FIG. 8 is a partial side-sectional view of the pipe and a perspective of components therein taken at about 15° showing the head member against an annular ridge in the restricting flange.

FIG. 1 shows the device which includes a hollow inlet pipe 18 and an outlet pipe 14, through which gas will pass when a user places outlet pipe end 16 between the lips and inhales. Although the design of the device illustrated in FIG. 1 and further described hereinafter is intended for use by inhaling through the outlet end 16 of pipe 14, which serves as a mouthpiece, the device may also be used for exercising the lungs exhaling and making slight modification as will be explained hereinafter. As used herein, the term gas shall mean breathable oxygen containing gaseous mixtures, normally atmospheric air, as well as exhaled gas.

The gas handling and directing portion of the device comprises valve assembly 12 incorporating a valve housing 40, shown partially cut away and a valve body 30 which is received in the hollow cavity of the valve housing. This valve assembly is shown further in FIGS. 2-7 illustrating a variety of different positions of the valve body in order to better understand its functioning characteristics and means for handling the gas as it passes through the valve assembly. Specifically, inspired gas entering an opening at end 43 of inlet pipe 18 is directed through the pipe and past inlet port 24 on valve housing 40. As previously explained, the valve housing is hollow or has a hollow cavity in which the valve body is received. The valve body may be press fit into housing cavity so that there will be substantially no air leakage between the exterior cylindrical wall of the valve body and the interior cylindrical valve housing wall. However, the fit between the housing and body walls are such that the valve body can be rotated so as to vary the volume of gas passing through outlet port 26.

Observing also FIGS. 2-7, valve body 30 includes a first passageway 32 which communicates between inlet port 24 and outlet port 26 when the valve body is so aligned. This can be observed particularly in FIG. 2 which shows the valve body as it is viewed from the position of the outlet port with the valve housing shown in section across its diameter along a plane normal to the plane of observation. FIGS. 1, 2, 3, 4 and 5 all show the valve body positioned so that divider wall 28, which separates first passageway 32 from second passageway 34, is disposed approximately centrally in relation to outlet port 26, in which position approximately equal volumes of inspired gas will be directed into the respective first and second passageways. This is shown particularly in FIG. 5 which illustrates a top sectional view through both the valve housing and valve body, approximately horizontally across the diameter of both the inlet and outlet ports 24 and 26, respectively. The valve body may be solid with the passageways cut out, or it may be of a hollow construction with the passageway molded or otherwise formed.

Figure 2:
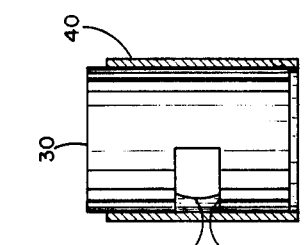
FIGS. 2, 3, and 4 are side views, partially in section, illustrating different positions of the valve body.
Figure 3:
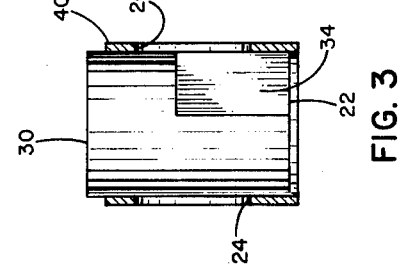
Figure 4:
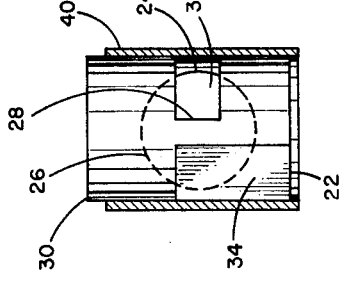

The bottom of the valve housing is open so that second passageway 34 is open to by-pass port 22. Thus, when the user inspires through the device, communication of second passageway 34 with outlet port 26 will cause air to be pulled into by-pass port 22, and through the second passageway and outlet port. Likewise, where first passageway 32 communicates with both inlet port 24 and outlet port 26, inspired air is directed through the valve body to outlet port 26, and on through outlet pipe 14. It is the gas passing through the first passageway that is detected or monitored as will be explained hereinafter. FIG. 3 shows the side view of the valve body and sectioned valve housing. FIG. 4 illustrates the back surface of valve body 30 with outlet port 26 being observed through first passageway 32 as the valve body is viewed from the position of the inlet port.

Figure 5:
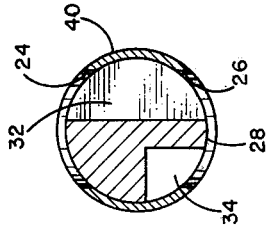
FIGS. 5, 6, and 7 are top sectional views illustrating different positions of the valve body in the valve assembly housing.
Figure 6:
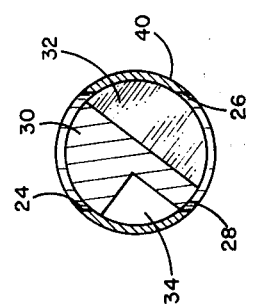
Figure 7:
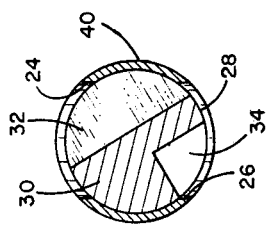

FIGS. 5-7 illustrate different positions that might be used for varying the volume of inspired gas passing from inlet port 24 to outlet port 26. Observing FIGS. 2 and 5, in the valve body position shown, with separator wall 28 located approximately mid way across inlet port 24, about one-half of the inspired gas will flow through first passageway 32 outlet port 26 and on to the patient, and approximately one-half of the inspired gas will be drawn through by-pass port 22 and into second passageway 34. In FIG. 6, with valve body 30 turned so that divider wall 28 meets the left edge of port 24, no gas can pass into second passageway 34. Thus all inspired gas must pass through first passageway 32 where it is directed on through outlet port 26 and the outlet pipe. In FIG. 7, valve body 30 is turned relative to the inlet and outlet ports so that the majority of inspired gas is entrained through the by-pass port and second passageway 34 whereas only a small amount of gas can pass between the right edge of inlet port 24 and divider wall 28.

Observing further FIG. 1, there is shown the means for monitoring inspired gas passing into inlet pipe 18. Located within pipe 18 is a plunger shaft 46 having an enlarged head member 44. Also located within pipe 18 is a restricting flange 42 which projects interiorly within the inlet pipe so as to provide a narrower restriction adjacent the head member 44. Preferably, the shaped interior surface of the restricting flange will be of the same shape as the exterior surface of the head member, usually both being substantially circular with the diameter across the restricting flange opening being somewhat larger than the diameter of the head member so as to allow the passage of gas therebetween. The restricting flange preferably includes an annular ridge 41 against which the surface of head member 44 will abut when in a rest position. The plunger is also provided with a biasing means for urging the plunger rod and head member to a rest position within the restricted area and against ridge 41. Such a biasing member may be conveniently provided by an elastic band 45 or similar equivalent means which is secured to plunger rod 46. The ends of the elastic band may be anchored at any suitable location or position within the outlet pipe. It should be understood that any other equivalent means for providing bias for the plunger rod will be suitable. The ridge 41 is preferably positioned so that it will urge the head member toward the inlet port 24 thereby keeping some tension on the elastic at all times, even in the rest position. This will assure that the head member will always return to the same rest position against the ridge and concomitantly cause correct positioning of detected plunge rod end as hereafter explained.

At the end 43 of inlet pipe 18 is positioned an electronic sensing collar or harness 50 which detects the exposure of plunger rod end 47 as it extends beyond inlet pipe end 43. The end 47 of the plunger rod may be coated or otherwise provided with some detectable material or composition, the presence of which past the end 43 of the inlet pipe interrupts the electronic field around the interior collar surface and thus adjacent the end of the outlet pipe.

In operation, the device functions by detecting the movement of air along inlet pipe 18 as it displaces head member 44 and concomitantly forces end 47 of plunger rod 46 inwardly past end 43 of the inlet pipe. The absence of the plunger rod end 47 is detected by the electronic detecting collar as the plunger rod end passes out of the electronic field created within and defined by the interior collar wall. In the example shown, such a field is created between the circumferential collar wall, but this collar shape is not necessarily critical or limited to that shown. Also illustrated is a securing ring 36 to which are attached support arms 52 for placing and securing the electronic collar 50 onto the end of the inlet pipe. Also shown are conductive wires 49 for providing the electronic field for the collar 50 as well as for electronic transmissions between the collar and electronic monitoring and counting equipment 35.

Specifically, in utilizing the device, the patient performing an exercise simply inhales through the opening end 16 of outlet pipe 14. The difficulty of the exercise is proportional to the ratio of the area of the openings of the first passageway and the second passageway exposed to the outlet port. Thus, the valve position shown in FIG. 5 will result in a more difficult exercise than that shown in FIG. 6 because in the former, less air will be drawn through the inlet pipe on inspiration as compared to the position shown in FIG. 6. However, the valve position of FIG. 7 will result in an even more difficult exercise because the relatively large area of passageway 34 exposed to outlet port 26 as compared to the small exposed area of passageway 32. The user or therapist will adjust the valve body by turning or rotating it within the valve housing so as to expose the desired area ratios of the first and second passageways to the outlet port to meet the initial exercise demands or requirements. Knob 25 or other similar means may be attached to or formed with the valve body which may be grasped by the user for turning the valve body. Once the valve has been adjusted to the proper positions with the user inspiring into the outlet pipe, gas passing into the inlet pipe will be forced between the edge of head member 44 and the surface of restricting flange 42. The force of this air passing this restriction will cause head member 44 to be forced inwardly, toward the valve assembly, as will plunger rod 46, against the bias of biasing member 45. Concomitantly, plunger rod end 47 will be forced out of the electronic sensing field of sensing collar 50. This uninterrupted field will then be detected.

Preferably, conducting wires 49 will cooperate with a timing and counting device which will both count the number of times that the electronic field is uninterrupted by the absence of the end of the plunger rod as well as the length of time that the rod is absent from the field. The purpose for such a feature is to count the number of inspirations during the exercise whereby the results may be observed by the user and a therapist or physician. In addition, the device may also count and display the time of each inspiration where not only the number of inhalations is important in any exercise but also the longevity of each. Preferably, such a monitoring device is also adjustable so as to vary the length of time of an inspiration before the device will count that inspiration in the exercise. Thus, for example, observing further FIG. 1, there is shown a counting and sensing device 35 having a numeral display window 38 and lights 31 and 33. During operation the display window 38 will show the number of completed inspirations in the exercise. Light 31 will respond when the patient begins to inhale, as gas is drawn into the inlet pipe and displaces the plunger head, and light 33 will be turned on after the patient has inhaled for a selected length of time. Thus, when light 33 glows the patient will know that he has satisfied the minimum time requirement during that inspiration and the inspiration will then be counted and displayed in window 38. Again, preferably the minimum length of time for each inspiration may be varied by an adjustment on the device to suit different user abilities. Moreover, as previously explained, the difficulty of the exercise may be varied significantly by adjusting the valve body so as to allow more or less gas to pass into second passageway and by-pass the first passageway thus increasing the difficulty of that exercise.

Although the valve body has been illustrated in the preferred embodiment as being rotatable within a valve housing and received in a hollow valve cavity therein for varying the difficulty of the exercise, other equivalent means for achieving the same function such as a sliding valve body, and the like may be used so long as the intended purpose is achieved. Moreover, the reciprocating and bias plunger and head member cooperating with the restriction flange may also be modified by utilizing any other suitable equivalent means for detecting the passage of air within the device which is to be monitored during the exercise. Further, the valve housing and inlet and outlet pipes are also formed so as to be easily assembled. Further, it may be desirable to utilize different outlet pipe sections in constructing the device which sections can be fitted together so as to simplify assembly in placing the plunger rod and head within the outlet pipe and securing the biasing member 45 as previously discussed.

Again, although the device has been described herein as used primarily for inspiration exercise, it may be instead used for expiration as well. This may simply require slight modification such as by using a shorter plunger rod the presence of which will be detected past the end 43 of pipe 18 as it is forced outwardly by exhaled gas. The head member 44 would also be biased against the opposite side of ridge 41 from that shown. In such use, the relative exercise difficulty will be proportional to the same ratio of expose of the first and second passageway openings to port 24. By-pass gas exhaled by the user would pass into second passageway 34 and be exhausted through by-pass port 22 whereas gas passing through first passageway 32, port 26, and pipe 18, which will be monitored as described above. These as well as other modifications of the device within the purview of the invention will be understood by those skilled in the art.

We claim:

1. A device for exercising the lungs comprising:
    a valve housing having a cavity, a gas inlet port, a gas outlet port, and a gas by-pass port, each communicating with said cavity;
    a valve body moveably received in said cavity having a first passageway for communicating between said gas inlet and outlet ports, and a second passageway for communicating between said gas outlet port and said gas by-pass port;
    whereby movement of said valve body provides selective alignment of said first and second passageways with said ports for determining the respective volumes of gas passing through said inlet port and said by-pass port;
    a gas inlet pipe communicating with said valve housing through said gas inlet port;
    a gas outlet pipe communicating with said valve housing through said gas outlet port;
    a moveable member moved by gas passing through said gas inlet and outlet pipes; and means for monitoring the movement of said moveable member for counting sequential inspirations or expirations through the device.

2. The device of claim 1 including a mouthpiece secured to said gas outlet pipe.

3. The device of claim 1 including a chamber in said gas inlet pipe in which said moveable member is received, whereby said moveable member is moved by gas passing along said inlet pipe and through said chamber.

4. The device of claim 3 wherein said moveable member comprises a reciprocating shaft having a head member against which gas passing through said chamber is directed to displace said shaft and which displacement is detected by said monitoring means.

5. The device of claim 4 wherein said chamber includes a restricted passageway having a greater cross-sectional dimension than said head member whereby said gas passing through said chamber passes between said restricted passageway and said head member.

6. The device of claim 4 including biasing means for urging said reciprocating shaft to a rest position against the flow of said gas through said chamber.

7. The device of claim 6 wherein in said rest position said head member is disposed in said restricted passageway.

* * * * *